United States Patent
Taylor et al.

(10) Patent No.: US 6,887,677 B1
(45) Date of Patent: May 3, 2005

(54) COMPOUNDS AND METHODS FOR IDENTIFYING COMPOUNDS WHICH INHIBIT A NEW CLASS OF ASPARTYL PROTEASES

(75) Inventors: Ronald K. Taylor, Lebanon, NH (US); Christian F. LaPointe, Nashua, NH (US)

(73) Assignee: Trustees of Dartmouth College, Hanover, NH (US)

( * ) Notice: Subject to any disclaimer, the term of this patent is extended or adjusted under 35 U.S.C. 154(b) by 523 days.

(21) Appl. No.: 10/030,808

(22) PCT Filed: Jul. 11, 2000

(86) PCT No.: PCT/US00/18775

§ 371 (c)(1),
(2), (4) Date: May 3, 2002

(87) PCT Pub. No.: WO01/04277

PCT Pub. Date: Jan. 18, 2001

Related U.S. Application Data

(60) Provisional application No. 60/143,355, filed on Jul. 12, 1999.

(51) Int. Cl.$^7$ .............................. C12Q 1/37; C12N 9/52; C07H 21/04
(52) U.S. Cl. ........................ 435/23; 435/220; 536/23.7
(58) Field of Search ................... 423/23, 230; 536/23.7

(56) References Cited

U.S. PATENT DOCUMENTS

| | | |
|---|---|---|
| 5,872,210 A | 2/1999 | Medabalimi ................. 530/327 |
| 2002/0016296 A1 | 2/2002 | Haass et al. ................... 514/16 |

FOREIGN PATENT DOCUMENTS

| | | |
|---|---|---|
| DE | 199 02 550 A1 | 7/2000 |
| WO | WO 95/12408 | 11/1995 |
| WO | WO 00/43505 | 7/2000 |

OTHER PUBLICATIONS

Billich et al., "Synthetic Peptides as Substrates and Inhibitors of Human Immune Deficiency Virus–1 Protease", J. Biol. Chem. 1988 263(34):17905–17908 XP–002224206.
Humblet et al., "Characterization of two structurally novel HIV–1 protease inhibitors identified by rational selection", Antiviral Research 1993 21:73–84 XP009002114.
Kaufman et al., "Processing of TCP pilin by TcpJ typifies a common step intrinsic to a newly recognized pathway of extracellular protein secretion by gram–negative bacteria", Genes & Development 1991 5:1834–1846 XP009002002.
Kick et al., "Structure–based design and combinatorial chemistry yield low nanomolar inhibitors of cathepsin D", Chemistry & Biology 1997 4(4):297–307 XP–002065985.
Sohail et al., "Thermostabilization of carboxymethylcellulase from *Aspergillus niger* by carboxyl group modification", Biotechnology Letters 1997 19(4):325–329 Database accession No. PREV19979952378 XP–002224404.
Strom et al., "Posttanslational processing of type IV prepilin and homologs by PilD of *Pseudomonas aeruginosa*", Methods in Enzymology 1994 235:527–540 Database accession No. NLM8057924 XP002224403.
Toogood et al., "A pepstatin–insensitive aspartic proteinase from a thermophilic *Bacillus* sp.", Biochem. J. 1995 307:783–789 xP009002116.
Alm et al., "Genes involved in the biogenesis and function of type–4 fimbriae in *Pseudomonas aeruginosa*", Gene 1997 192:89–98.
Darzins et al., "Molecular genetic analysis of type–4 pilus biogenesis and twitching motility using *Pseudomonas aeruginosa* as a model system—a review$^1$", Gene 1997 192:109–115.
Filloux et al., "GSP–dependent protein secretion in Gram–negative bacteria:the Xcp system of *Pseudomonas aeruginosa*", FEMS Microbiology Reviews 1998 22:177–198.
LaPointe et al., "The Type 4 Prepilin Peptidases Comprise a Novel Family of Aspartic Acid Proteases", J. Biol. Chem. 2000 275 (2):1502–1510.
Russell et al., "The PilE gene product of *Pseudomonas aeruginosa*, required for pilus biogenesis, shares amino acid sequence identity with the N–terminal of type 4 prepilin proteins", Molecular Microbiology 1994 13(6):973–985.
Database Swiss–Prot38. Accession No. P27717 and Q56668. "Type 4 prepilin–like proteins leader peptide processing enzyme", Kaufman et al. 1992.

*Primary Examiner*—Robert A. Wax
(74) *Attorney, Agent, or Firm*—Licata & Tyrrell P.C.

(57) ABSTRACT

Compounds and methods for designing and identifying compounds which inhibit TFPP-like aspartyl protease enzymes by targeting the aspartic acid residues of the active site or mimicking peptides corresponding to the region surrounding the substrate's cleavage site are provided. Agents identified as inhibitors of TFPP-like aspartyl proteases such as type 4 prepilin peptidases are expected to be useful as anti-bacterial agents and in inhibiting development of drug resistant strains of bacteria.

11 Claims, 2 Drawing Sheets

COMPOUNDS AND METHODS FOR IDENTIFYING COMPOUNDS WHICH INHIBIT A NEW CLASS OF ASPARTYL PROTEASES

This application claims the benefit of provisional application Ser. No. 60/143,355 filed Jul. 12, 1999.

This invention was supported in part by funds from the U.S. government (NIH Grant No. RO1 AI25096 and F31 AI09635) and the U.S. government may therefore have certain rights in the invention.

FIELD OF THE INVENTION

A family of transmembrane protease enzymes has now been identified which comprise two critical aspartic acid residues on the same side of the membrane at their active cleavage site. Members of this family of protease inhibitors can be identified by a consensus sequence at the C-terminal aspartic acid residue comprising G-X-G-D-(F or V or P or K or I or L or Y). The mechanism of action of these aspartyl proteases is exemplified herein through the bacterial protease type 4 prepilin peptidase (TFPP). Accordingly, these proteases are referred to herein as TFPP-like aspartyl proteases. The present invention relates to compositions and methods for identifying and designing compositions which inhibit TFPP-like aspartyl proteases by targeting the aspartic acid residues of the enzymatic active site or mimicking a region surrounding the cleavage site of a TFPP-like aspartyl protease substrate. These compositions are expected to be useful in inhibiting the activity of TFPP-like aspartyl proteases involved in diseases and infections.

BACKGROUND OF THE INVENTION

The development of the first anti-infective or anti-bacterial agents in the early 1900's and the success seen with their use led to the development of hundreds of new compounds to fight the wide variety of bacterial organisms. Most people have had exposure to these drugs at some point in their life, with the majority of situations resulting in a rapid cure of the bacterial infection with relatively few side effects. However, human morbidity and mortality due to bacterial infections has become a major concern today due to the dramatic increase in the frequency of infections caused by bacteria that are resistant to most, if not all, of the available anti-bacterial agents. This increase in drug-resistant pathogens has led to an ever-increasing need for new drugs with new mechanisms of action.

Anti-bacterial agents are developed by identifying unique targets not present in mammalian cells and then designing a drug to exploit that difference such that the bacterial cells are killed or neutralized while mammalian cells are left intact and unaffected. The goal of successful anti-bacterial drug therapy is to limit toxicity in the patient while maximizing the ability of the drug to invade the bacterial cells and neutralize those cells as selectively as possible. The major classes of anti-bacterial drugs available today target a variety of different cellular components and functions of bacteria such as the cell wall, protein synthesis, cell metabolism, DNA synthesis, and the bacterial cell membrane. Each of these target cellular components or functions is related in some way to the disease process of bacterial infections that involves first colonization of the bacteria, invasion of host cells, production of cellular toxins or inflammatory agents, and a host response to those toxins or agents.

A fundamental process of all living cells, including bacteria, is the secretion of proteins across membranes. The majority of proteins that are secreted are synthesized as a precursor with an N-terminal signal sequence (or leader peptide) of about 16–24 amino acids in length. This leader sequence serves to promote recognition of the protein by the secretory apparatus of the cell and facilitates movement across the membrane. The leader sequence is subsequently processed by a leader peptidase to remove the sequence and allow release of the mature or active protein. Recent research has indicated that in the case of bacteria, there are several systems for secreting proteins and some of these systems have unique leader peptidases associated with their cognate secreted proteins. One of these systems is known as the type 2 secretion system which promotes extracellular secretion of bacterial factors such as toxins and colonization pili that are the hallmarks of the mechanisms that promote virulence of pathogenic bacteria. Pili mediate the binding of bacteria to host tissues and most pili are composed of a major protein subunit that polymerizes to form a pilus.

The type 2 secretion systems of most bacteria involve a type 4 pilin for colonization pilus formation and type 4 pilin-like proteins for secretion of toxins and other factors associated with bacterial virulence and destruction of host tissue and enhancement of bacterial growth in the host. Highly related type 4 pili serve as the major colonization factors for up to 50 different gram-negative bacterial species and type 4 pilin-like proteins have been found for a growing number of gram-positive bacteria as well. Type 4 pili are composed of a polymerized structure of type 4 pilin. The pilin is synthesized as a prepilin with a leader peptide that is very different from those of typical secreted proteins. A type 4 specific leader peptidase is required to process a type 4 prepilin leader sequence to allow secretion of the mature protein. Importantly, this secretion system including the type 4 leader peptidase itself is only found in bacteria and is not present in humans or other potential hosts of infection. Furthermore, mutating the type 4 prepilin peptidase (TFPP) renders the bacterium avirulent (March and Taylor 1998. Mol. Microbiol. 29:1481–1492).

The type 4 signal peptide is highly conserved across all type 4 prepilin or prepilin-like proteins and is composed of 6 to 25 highly charged amino acids at the N-terminus followed by approximately 20 predominately hydrophobic amino acids. Cleavage occurs between the two domains immediately C-terminal of an invariant glycine and before the new N-terminal amino acid that is usually a methionine or a phenylalanine. Unlike cleavage of standard signal peptide by signal peptidase I, wherein the cleavage occurs on the periplasmic side of the inner membrane, processing by a type 4 peptidase occurs on the cytoplasmic side of the inner membrane (Strom and Lory, 1993. Ann. Rev. Microbiol. 47:565–596). Previous mutational analysis and protease inhibitor evidence from studies of pilD of *Pseudomonas aeruginosa* and protein alignment analysis of the type 4 peptidase family suggested two pairs of cysteines in cytoplasmic domain 1, the largest cytoplasmic domain, to be involved in the protease active site of the enzyme (Strom et al. 1993. Proc. Natl. Acad. Sci. USA 90:2404–2408). These data resulted in the categorization of type 4 prepilin peptidase (TFPP) family as a type of cysteine protease (Strom et al. 1994. Meth. Enzymol. 235:527–540).

However, subsequent studies have shown the two cysteine pairs to be lacking in XpsO, a type 4 prepilin peptidase of *X. campestris*. In fact, several type 4 prepilin peptidases, among the approximately 27 that have been identified and cloned, do not have the conserved cysteines in their protein sequence but still function to cleave the type 4 signal peptide.

In the present invention a specific domain of type 4 prepilin peptidase that is essential for cleavage activity has now been identified to the resolution of two specific amino acids. Identification of this domain has facilitated the identification of specific inhibitors of the protease activity of type 4 prepilin peptidase as well as other TFPP-like aspartyl proteases which utilize this same cleavage mechanism.

SUMMARY OF THE INVENTION

Using mutant constructs of TcpJ, residues essential for cleavage activity of the bacterial protease type 4 prepilin peptidase (TFPP) have now been identified as two aspartic acid residues. Thus, useful anti-bacterial agents targeted to these residues can now be designed to inhibit the cleavage activity of type 4 prepilin peptidase which is essential to growth of bacteria in a host. Further, a consensus sequence at the C-terminal aspartic acid residue comprising G-X-G-D-(F or V or P or K or I or L or Y) has been identified so that TFPP-like aspartyl proteases of organisms other than bacteria, including humans, which comprise this novel active site and utilize a cleavage mechanism similar to that exemplified herein for type 4 prepilin peptidase can be identified. For purposes of the present invention, proteases of this new family which are transmembrane protease enzymes comprising two critical aspartic acid residues on the same side of the membrane at their active cleavage site, wherein a consensus sequence at the C-terminal aspartic acid residue comprising G-X-G-D-(F or V or P or K or I or L or Y) is present, are referred to herein as "TFPP-like aspartyl proteases". This term is meant to be inclusive of type 4 prepilin peptidases.

Accordingly, an object of the present invention is to provide a method of designing inhibitors of TFPP-like aspartyl proteases which comprises synthesizing compounds which target the aspartic acid residues of the enzymatic active site of the TFPP-like aspartyl protease or mimic a region surrounding the cleavage site of the TFPP-like aspartyl protease substrate and inhibit cleavage activity of the protease. Also provided in the present invention are methods of selecting and screening compounds for inhibitory activity of these TFPP-like aspartyl protease enzymes. Compounds identified as inhibitors can be used to modulate activity of TFPP-like aspartyl proteases involved in disease and infection. In one embodiment, compounds identified as inhibitors are used as anti-bacterial agents in the inhibition of type 4 prepilin peptidases.

Thus, another object of the present invention is to provide new anti-bacterial agents which comprise compounds which target the aspartic acid residues of type 4 prepilin peptidase and inhibit cleavage activity of this peptidase. As will be obvious to those of skill in the art upon this disclosure, such agents are also expected to be useful in inhibiting other TFPP-like aspartyl protease enzymes of this family which utilize the same cleavage mechanism as described herein for type 4 prepilin peptidase and/or contain the same active site. Other TFPP-like aspartyl protease enzymes of this family can be identified routinely by those of skill in the art based upon the presence of the consensus sequence comprising G-X-G-D-(F or V or P or K or I or L or Y) at the C-terminal aspartic acid residue of the enzymatic active site.

Another object of the present invention is to provide methods of inhibiting activity of TFPP-like aspartyl protease enzymes via administration of a compound which targets the aspartic acid residues of the enzymatic active site of the TFPP-like aspartyl protease or mimics a region surrounding the cleavage site of the TFPP-like aspartyl protease substrate and inhibits cleavage activity of the protease. In one embodiment of the present invention, bacterial infection in a host is inhibited by administering to a host infected with the bacteria a compound which targets the aspartic acid residues of type 4 prepilin peptidase and inhibits cleavage activity of this peptidase.

Also related to this embodiment of the present invention are methods and compositions for decreasing development of drug resistant strains of bacteria through coadministration of a compound which targets the aspartic acid residues of type 4 prepilin peptidase and inhibits cleavage activity of this peptidase with a second known therapeutically effective anti-bacterial agent.

Another object of the present invention is to provide TcpJ mutant constructs useful in defining the active cleavage site of type 4 prepilin peptidase and in X-ray crystal structure analysis of this enzyme.

Yet another object of the present invention is to provide a homologous type 4 prepilin peptidase gene identified in *Staphylococcus aureus*.

DETAILED DESCRIPTION OF THE INVENTION

Figure 1:
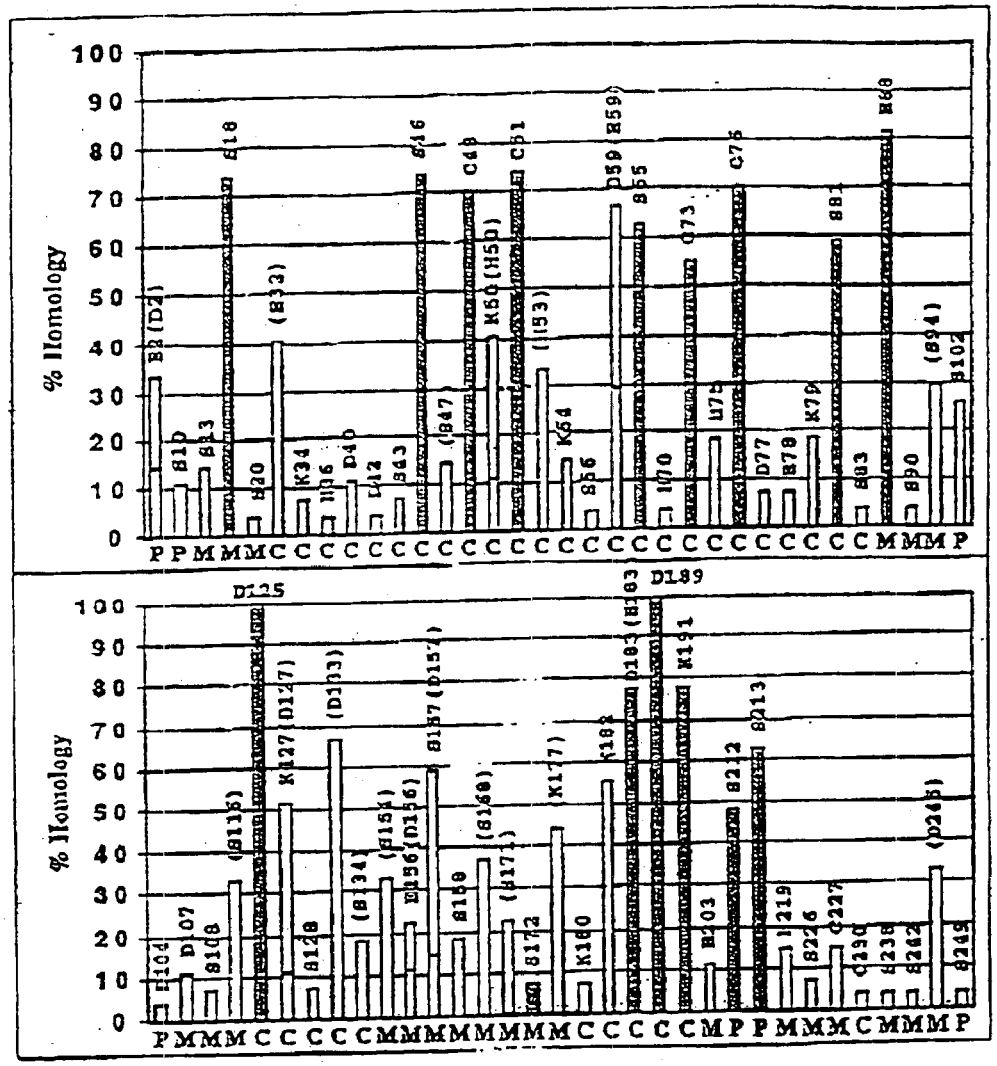
FIG. 1 is a bargraph showing the percent of conserved homology of potential protease active site residues from 27 type 4 prepilin peptidase homologs. Conserved residues which do not exist in TcpJ are in parenthesis and are designated with the relative position in TcpJ. Predicted membrane topology is indicated by C (cytoplasmic), P (periplasmic) or M (transmembrane) below each residue. Shaded bars indicate the conserved residues which were altered in experiments described herein. Alignment was performed in DNASTAR MegAlign using the Clustal method.

The type 4 prepilin peptidase is found only in bacteria and is responsible for the cleavage and N-methylation of a large number of secreted proteins known as type 4 prepilins, or prepilin-like proteins, that have a type 4 signal peptide at their N-terminus. The cleavage of the type 4 signal peptide is a necessary step to secretion of the type 4 prepilin. Prepilin-like proteins are involved in DNA competence and/or uptake in *B. subtilis*, in phage morphogenesis in *E. coli*, and partially comprise the type 2 secretion system which is the main terminal branch of the general secretory pathway in gram negative bacteria (Pugsley, 1993. *Microbiology Reviews* 57(1):50–108). Type 4 pili serve as the major colonization factors for up to 50 different gram-negative bacterial species. Therefore, agents which interfere with, or inhibit, activity of type 4 prepilin peptidase are expected to be useful as anti-bacterial drugs and in the identification of anti-bacterial drugs. Further, given the role of prepilin-like proteins in DNA uptake, particularly in gram-positive bacteria (Dubnau, D. 1997. *Gene*

192:191–198; Wolfgang et al. 1999. *Molecular Microbiology* 31(5):1345–1357), it is believed that coadministration of these agents with a second anti-bacterial agent will inhibit uptake of antimicrobial agent resistance gene thereby reducing development of drug resistant strains of bacteria.

It has now been found that type 4 prepilin peptidase, specifically TcpJ, a type 4 prepilin peptidase of *Vibrio cholerae*, is a non-pepsin-like acid protease. A homologous gene has also now been identified in *Staphylococcus aureus*, a bacterium which is very difficult to treat due to its ability to become resistant to drugs. The nucleic acid sequence encoding this peptidase in *Staphylococcus aureus* is depicted as SEQ ID NO:1. The amino acid sequence of this *Staphylococcus aureus* peptidase is depicted as SEQ ID NO:2. Contrary to prior art suggestions of cysteine residues being involved in the protease active site of this enzyme ((Strom et al. 1993. *Proc. Natl. Acad. Sci. USA* 90:2404–2408), residues essential for cleavage activity of this peptidase have now been identified as two aspartic acid residues. Further, a consensus sequence at the C-terminal aspartic acid residue comprising G-X-G-D- (F or v or P or K or I or L or Y) has been identified so that TFPP-like aspartyl proteases of organisms other than bacteria, including humans, which comprise this novel active site and utilize a cleavage mechanism similar to that exemplified herein for type 4 prepilin peptidase can be identified. Accordingly, this peptidase is part of a novel subclass or family of non-pepsin-like acid proteases, referred to herein as TFPP-like aspartyl proteases. For purposes of the present invention, by "TFPP-like aspartyl protease" it is meant a transmembrane protease enzyme comprising two critical aspartic acid residues on the same side of the membrane at its active cleavage site, wherein a consensus sequence at the C-terminal aspartic acid residue comprising G-X-G-D-(F or V or P or K or I or L or Y) is present. This term is meant to be inclusive of type 4 prepilin peptidases.

Further, it has now been demonstrated that agents which target the aspartic acid residues of this active site inhibit the cleavage activity of proteases in this new family. For example, inhibition of type 4 prepilin peptidase was accomplished by contact of the peptidase with the combination of EDAC (1-ethyl-3-(3-dimethylaminopropyl)carbodiimide hydrochloride) and glycinamide, a combination of compounds known to inhibit non-pepsin-like acid proteases. Using the knowledge of this target area within the peptidase sequence essential for cleavage activity, additional inhibitors of this class of protease enzymes can also be identified. For example, inhibitors designed to target the aspartic acid residues, D125 and D189, which are essential to the cleavage activity of type 4 prepilin peptidase, can be synthesized for se as anti-bacterial agents. Preferably, the inhibitors are transition state analogues or other compounds that modify or competitively inhibit the aspartic acid residues thereby preventing cleavage activity.

To determine the particular amino acids of aspartyl proteases such as TcpJ and other type 4 prepilin peptidases that act as the catalytic residues of the protease activity, the protein sequence alignment of 27 type 4 prepilin peptidases was examined for highly conserved amino acids which have the potential to be protease active site residues. All cysteines, serines, aspartic acids, histidines, lysines, and glutamic acids that represent consensus residues in these type 4 prepilin peptidases are shown in FIG. 1. Potential active site residues of TcpJ, regardless of the level of conservation, are also shown in FIG. 1.

Figure 2:
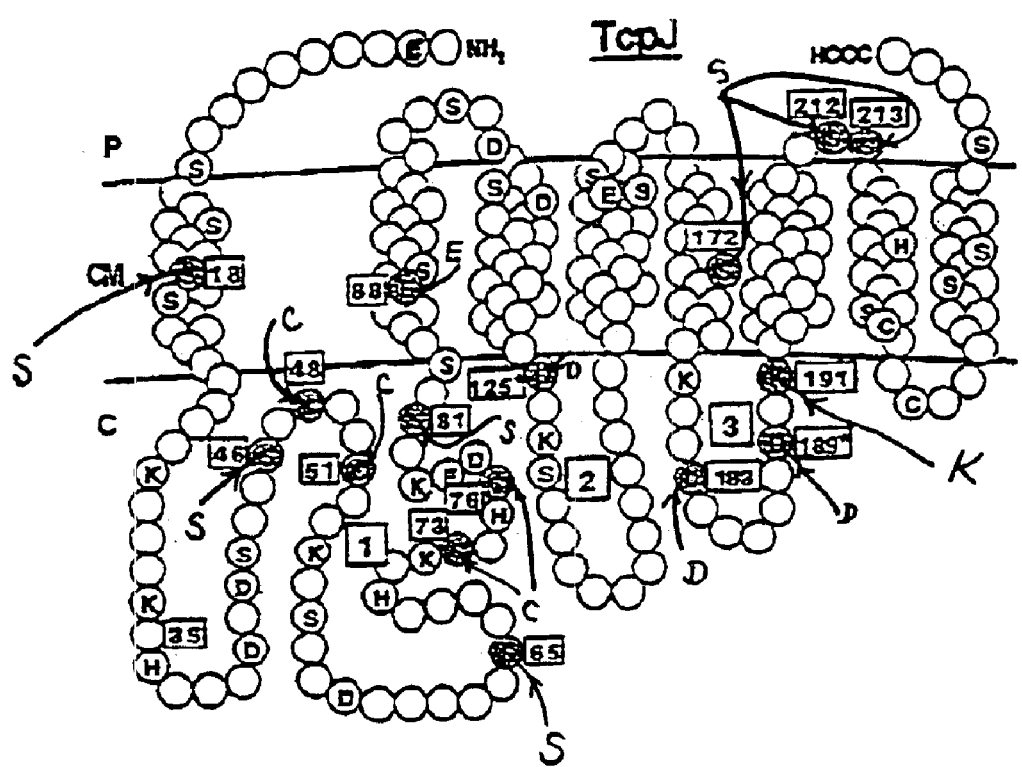
FIG. 2 is a predicted TcpJ membrane topology model. The predicted topology of TcpJ was deduced by comparison with OutO of *Erwinia carotovora* for which the membrane topology has been determined by the use of beta lactamase-fusions in outO. Cytoplasmic domains 1, 2 and 3 have been designated as well as C (cytoplasmic), P (periplasmic) and M (transmembrane) regions. All potential protease active sites (C, S, D, K, H, E) have been designated. Amino acids altered in experiments described herein are shaded and numbered by their position. Each critical active site residue, D125 and D189, is marked with a "*".

A mutational strategy was then used to determine the active site residues of type 4 prepilin peptidase of *Vibrio cholerae* (Genbank Accession No. M74708). The nucleic acid sequence of this gene is depicted herein as SEQ ID NO:3; the amino acid sequence of this peptidase is depicted as SEQ ID NO:4. Fifteen of the most highly conserved active site residues were mutated to either alanine or leucine in TcpJ, the type 4 prepilin peptidase of *Vibrio cholerae*. The residues selected included S18, S46, C48, C51, S65, C73, C76, S81, E88, D125, S172, D183, D189, K191, S212, and S213 (see FIG. 2). D125 and D189 were also mutated to N and E. D183 was mutated to N. Mutations at the selected positions of tcpJ were made in pCL10, a plasmid containing tcpJ and tcpA expressed from a lac promoter. These mutant constructs of the present invention were then introduced into *Vibrio cholerae* CL381, a classical 0395 with an insertional disruption in tcpJ and an in-frame deletion of vcpD conferring a complete inability to cleave TcpA. The resultant strains were grown under TCP-inducing conditions (LB pH 6.5, 30° C.). The resulting whole cell extracts were loaded on a SDS-PAGE gel and Western immunoblot was performed with antisera to TcpA. The results showed that D125A and D125N and D189A and D189N were the four mutants that displayed a complete loss of TcpJ activity. C48A and K191A showed some loss of activity while all other mutants did not show any loss of cleavage activity. The chemical and structural requirements of the reactive sites were further defined by substituting E at positions D125 and D189. Partial activity was maintained. Since the chemical nature of the D and E side groups are similar, it is believed that the side group chemistry is responsible for the cleavage activity of the peptidase. The chemical structure of D provides for the optimal reaction as compared with E.

*E. coli* amber suppressor strains were utilized to determine the activity of TcpJ peptidases with a number of amino acid substitutions at the 125 and 189 positions. An amber (TAG) site was individually engineered into the 125 and 189 positions of the pCL10 plasmid and the resultant constructs were introduced into the Amber-Lys, Amber-Leu, Amber-Gln, Amber-Ser, Amber-Tyr amber suppressor strains. The strains were grown to mid-logarithmic phase and whole cell extracts were examined for TcpA and TcpJ by Western immunoblot analysis. No amino acid substitution at either 125 or 189 exhibited any cleavage activity. The protein levels of TcpJ were all comparable to wild-type TcpJ.

TcpJ mutant activity was then assessed in an in vitro assay modeled after the in vitro peptidase assay devised for PilD of *P. aeruginosa* (Nunn, D. N. and S. Lory. 1991. *Proc. Natl. Acad. Sci. USA* 88:3281–3285). Crude preparations of TcpA-containing membranes from JM109 p3Z A and TcpJ-containing membranes from JM109 pCL9 were combined with cardiolipin and 5× assay buffer to commence cleavage of TcpA. After incubation of TcpA-containing membranes with approximately 0.5 μg of TcpA prepilin and increasing amounts of TcpJ-containing membranes, 1 unit of TcpJ activity was defined as the amount of TcpJ-containing membrane required to cleave 50% of 0.5 μg of TcpA prepilin in 1 hour. To determine the in vitro peptidase activity of 10 of the 16 TcpJ amino acid positions previously tested in vivo, single or multiple mutations representing each position were constructed in PCL9 and introduced into JM109. Membrane preparations of these *E. coli* strains which lack TcpA prepilin were combined in the in vitro peptidase assay with 0.5 μg of TcpA prepilin from TcpA-containing membranes. Western blot analysis demonstrated that mutations at positions D125 and D189 were completely defective for processing whereas all other TcpJ mutants tested had some peptidase activity except for C48A which showed no detectable cleavage activity. However, the C48A TcpJ protein degrades in vitro. The protein levels of all of the TcpJ mutants were comparable.

Since no residue was found in domain 1 that was an absolute requirement for TcpJ cleavage activity and because several type 4 prepilin homologs do not have domain 1 in their protein sequence, the requirement for domain 1 of TcpJ for cleavage activity was examined. A deletion was made in domain 1 from position 35 to 81 of TcpJ using pCL11 producing pCL11Δ35-81. The deletion of 35 through 81 removed the two cysteine pairs as well as the highly conserved serines at positions 46 and 65. This deletion therefore removes the residues that had been implicated in prepilin protease activity by PilD in *P. aeruginosa* (Strom and Lory, 1993. *Ann. Rev. Microbiol.* 47:565–596). pCL11Δ35-81 was introduced into JM109 and a membrane preparation was made and tested in the in vitro cleavage assay. This assay demonstrated that the TcpJ derivative expressed by the deletion retained activity. Western analysis using an anti-6His antibody confirmed that TcpJΔ35-81 was expressed and stable.

To determine the peptidase activity of TcpJΔ35-81 in vivo, pCL11Δ35-81 and the wild-type control pCL11 were introduced into J71K cells. The resultant strains were grown under TCP-inducing conditions. Whole cell extracts were examined by SDS-PAGE and Western immunoblot analysis with anti-TcpA antisera. The results showed that pCL11Δ35-81 can complement J71K similar to pCL11. TcpJΔ35-81 was able to restore TCP biogenesis to J71K cells as seen by TEM with a negative stain of the cultures. These data demonstrate that, contrary to prior art teachings (Strom, M. S. et al. 1993. *Proc. Natl. Acad. Sci. USA* 90:2404–2408), domain 1 is not required for type 4 prepilin cleavage or assembly of the resulting mature pilin into the pilus structure.

Thus, analysis of the protein sequence alignment of the type 4 prepilin peptidase family and the mutational strategy using the TcpJ mutant constructs coupled with the in vivo and in vitro assays confirmed that aspartic acid residues 125 and 189 make up the active site contrary to prior art teachings relating to cysteine pairs.

Based upon this identification, a standard TcpJ in vitro cleavage assay was performed with a number of chemical protease inhibitors to examine their ability to block TcpJ activity. Inhibitors were selected based upon this knowledge of the active site that were expected to effect or not effect this peptidase activity. The effect of chemical protease inhibitors on the peptidase activity of TcpJ was determined by incubating the inhibitor with an amount of membrane preparation known to contain 1 unit of activity of TcpJ for 30 minutes at room temperature. The TcpJ/inhibitor mixture was then tested for peptidase activity in the in vitro processing assay described in Example 3. Amounts of cleaved TcpA prepilin were quantitated and applied to the formula: % cleavage=(amount of cleaved TcpA in inhibition assay/amount of cleaved TcpA in no inhibitor control assay)×100. The inhibition of EDAC/Glycinamide is a two step protocol conducted in acidic conditions as described in Example 4. The inhibitors tested and the results are shown below in Table 1.

TABLE 1

The Effect of Chemical Inhibitors n TcpJ Cleavage In Vitro

| Chemical | Specificity | Suggested Concentration | Test Concentration | % Cleavage |
|---|---|---|---|---|
| E-64 | cysteine proteases | (1.4–28 μM)[a] (1–10 μM)[b] | 28 μM | 96 |
| Calpain inhibitor I | cysteine proteases | 45 μM | 45 μM | 87 |
| NEM | cysteine proteases | 1 mM[c] | 1 mM | 30 |
| Aprotinin | serine proteases | (0.01–0.3 μM)[a] | 0.3 μM | 100 |
| 3,4-DCI | serine proteases | (5–200 μM)[a] (5–100 μM)[b] | 100 μM 200 μM | 89 54 |
| Pefabloc SC | serine proteases | (0.4–4 mM)[a] | 2 mM 4 mM | 62 50 |
| Leupeptin | serine and cysteine proteases | 1 μM[a] (1–10 μM)[b] | 10 μM | 85 |
| PMSF | serine and cysteine proteases | (0.1–1 mM)[a] 3 mM[c] | 1 mM 3 mM | 98 68 |
| Phosphoramidon | metallopeptidases | (0.007–0.6 mM)[a] | 0.6 mM | 89 |
| EDTA-Na | metalloproteases | (0.5–1.3 mM)[a] | 1.3 mM | 100 |
| Bestatin | amino peptidase (metallo-) | 130 μM[a] | 130 μM | 81 |
| Pepstatin | aspartic proteases | 1 μM[a] (1–5 μM)[b] | 1 μM 10 μM 100 μM | 95 92 74 |
| EDAC/ Glycinamide | acid proteases | 0.1 M/1 M | 0.1 M/0.2 M | 0 |

[a]Boehringer Mannheim Corp.
[b]Prolysis, a protease and protease inhibitor Web server, Thierry Moreau
[c]Strom, 1993

The majority of the inhibitors tested had no effect. Included in this group were several inhibitors of cysteine proteases, serine proteases, metalloproteases, and one general commercially available aspartic acid protease inhibitor, pepstatin. Others had non-specific inhibitory effects such as NEM, which modifies cysteines and PMSF and Pefabloc SC which modifies serines. These inhibitors had partial effects at the higher test doses of the suggested concentrations. The complete insensitivity of TcpJ activity to pepstatin rules out the possibility that TcpJ is a pepsin-like aspartic acid protease. A combination of EDAC and glycine amide, which was selected based upon the active site determination described herein and its known ability to modify aspartic acid residues (Hoare, D. G. and Koshland, D. E. Jr. 1966. *J. American Chemical Society* 88(9):2057–8), inhibited TcpJ peptidase activity in the in vitro cleavage assay.

The ability to inhibit type 4 prepilin peptidase activity using peptides corresponding to the region surrounding the cleavage site of the prepilin substrate was also examined. For these experiments, a series of peptides were coexpressed in bacteria in which preTcpA could be processed to the mature form of the TcpJ prepilin peptidase. In order to express only a portion of preTcpA as a peptide, an amber (Am) mutation was created corresponding to position −1, +1, or +5 relative to the cleavage site of TcpA. Peptides were tested that were wild-type, or that contained mutations that would prevent cleavage by TcpJ. Their ability to function in trans to compete for TcpJ processing activity of the coexistent wild-type preTcpA was then assessed in a standard western immunoblot which detects precursor and mature forms of TcpA.

The mutations were made in a construct consisting of a 1 kb tcpJ fragment followed by a 2 kb tcpA fragment on the pALTER-Ex2 backbone. In each of these, tcpA contained the following mutations relative to its +1 processed amino acid:

| Plasmid | Amino Acid Substitution and Position | | | | | | | |
|---|---|---|---|---|---|---|---|---|
| | −3 | −2 | −1 | +1 | +2 | +3 | +4 | +5 |
| pCL1 (wild-type) | Gln | Glu | Gly | Met | Thr | Leu | Leu | Glu |
| pCL94 | Am | | | | | | | |
| pCL142 | Pro | | | | | | | |
| pCL144 | | | Am | | | | | |
| pCL159 | | | Am | | | | | |
| pCL161 | Pro | | | Am | | | | |
| pNPD-TCPA-5 | Pro | | Leu | Am | | | | |
| pNPD-TCPA-6 | Pro | | | Am | | | | |
| pNPD-TCPA-7 | | | Leu | | | | | Am |

To accomplish the analysis, these constructs were electroporated into JM109 cells. Antibiotic resistance on the pALTER-Ex2 backbone was to chloramphenicol, with the exception of CL1 which was to tetracycline. The wild-type TcpA for which processing was assessed was expressed from pGEM-3ZA/TCP-A which confers resistance to ampicillin. Expression of each peptide was driven via the T7 promoter and T7 RNA polymerase expressed upon infection of the cells with λDE3 phage.

Once transformed, the cells in the log-phase of growth were induced by infection with various concentrations of λDE3 phage and the whole-cell protein extract was run out on an acrylamide gel. Western immunoblotting with rabbit αTcpA showed both a leader-sequence processed mature TcpA band (identified relative to a 0395 TCP-A control) and a higher molecular weight unprocessed preTcpA band (identified relative to the pGEM3ZA control). In the experimental lanes, the ratio of unprocessed to processed forms increased with increasing expression of the peptide. These results were observed for every peptide examined, thus demonstrating that multiple peptide derivatives corresponding to the region surrounding the cleavage site of TcpA prepilin are capable of inhibiting the activity of the TcpJ type 4 prepilin peptidase. By "corresponding to" it is meant that the peptide is identical to the region surrounding the cleavage site of the target protein or substrate of the TFPP-like aspartyl protease or contains sufficient amino acid similarity such that the peptide mimics this region. As demonstrated herein, these peptide mimics inhibit the cleavage activity of the TFPP-like aspartyl proteases. In a preferred embodiment, these peptide mimics range in length from approximately 12 to 30 amino acids.

The combined results of the in vitro cleavage testing demonstrated that none of the highly conserved serines or cysteines are an active site residue of protease activity for TcpJ. However, D125 and D189 are demonstrated to be protease active site residues of TcpJ, thereby classifying TcpJ as a monomeric aspartic acid protease. The importance of these two residue sites is further supported by the data showing that all substitutions, except of E, at either positions 125 or 189 failed to restore any amount of protease activity indicating both aspartic acids are required for protease activity and further defining the chemical nature of the reaction. Therefore, TcpJ is a novel type of protease with two aspartic acid residues as the active site. This protease is completely resistant to pepstatin, a general aspartic acid protease inhibitor. The protein sequence analysis of the family of type 4 prepilin peptidases indicates that a common protease mechanism exists among these peptidases, regardless of the bacterial species tested. Further, it is believed that TFPP-like aspartyl proteases which utilize the same cleavage mechanism and/or contain the same active site as type 4 prepilin peptidase are present in other organisms, including humans. Such enzymes can be identified by the presence of the consensus sequence G-X-G-D-(F or V or P or K or I or L or Y) at the C-terminal aspartic acid residue.

In order to provide further evidence that the aspartic acid residues corresponding to D125 and D189 of TcpJ comprise the peptidase active site in all type 4 prepilin peptidases of the TFPP-like aspartyl protease subclass, mutations were also made to the putative protease active site of aspartic acid residues D147 and D212 of the other type 4 prepilin peptidase in *V. cholerae*, vcpD. Mutant D147A and D212A were constructed in vcpD on the plasmid pJM294. Mutant constructs D147A and D212A were examined for their ability to cleave the TcpA prepilin. Wild-type vcpD is known to be capable of at least partially cleaving this prepilin. In these experiments, wild-type, D147A and D212A forms of pJM294 were introduced into an *E. coli* JM109 strain carrying the TcpA-expressing plasmid pRTH3G7. Strains were grown to midlog phase; whole cell protein extracts were made from the cultures; and the extracts were examined by SDS-PAGE and western immunoblot analysis with anti-TcpA antiserum. Wild-type vcpD cleaved the TcpA prepilin completely under these conditions. In contrast, no cleavage occurred in the D147A and D212A mutants. An analogous result was seen with the cleavage of a natural substrate of vcpD, the type 4 prepilin-like protein EpsI. In these experiments, wild-type, D147A and D212A forms of pJM294 were introduced into JM290, an *E. coli* JM109 strain carrying the EpsI(6)His-expressing plasmid, pJM290. Strains were grown to midlog phase under the induction of 1 mM IPTG in order to express EpsI(6)His. Whole cell protein extracts were made from the cultures and examined by SDS-PAGE and western immunoblot analysis using the Tetra-His monoclonal antibody to detect the c-terminally 6-His epitope tagged EpsI. Wild-type VcpD was able to completely cleave EpsI from the precursor form to the mature form whereas the mutants were unable to perform this cleavage. These experiments thus demonstrate that alanine substitutions at D147 and D212, the aspartic acid residues in VcpD which correspond to protease active site D125 and D189 of TcpJ, completely eliminate peptidase activity. Thus, it is believed that these two residues comprise the active site of all members of the type 4 prepilin peptidase enzyme family. Accordingly, by targeting the active site identified herein as comprising two aspartic acid residues, one of skill can identify compounds capable of inhibiting activity of type 4 prepilin peptidases and other TFPP-like aspartyl proteases which utilize this same cleavage mechanism and/or contain the same active site. These compounds are expected to be useful as inhibitors of TFPP-like aspartyl proteases. In one embodiment, these compounds can be used as anti-bacterial agents in the inhibition of the type 4 prepilin proteases. One example of a method for identifying such inhibitors comprises determining the inhibitory activity of a test compound in an in vitro cleavage assay. In one embodiment of this assay, a bacterial cell membrane preparation which expresses type 4 prepilin peptidase is incubated with a test compound. The amount of cleavage activity in the preparation in the presence of the test compound is then compared to cleavage activity in a preparation which does not contain the test compound. Test compounds which decrease or inhibit cleavage activity are inhibitors of type 4 prepilin peptidase as well as other TFPP-like aspartyl proteases. For example, using this method, EDAC in combination with glycine amide was identified as an inhibitor of type 4 prepilin peptidase. In addition, peptides corresponding to the region surrounding the cleavage site of the prepilin substrate were also demonstrated to be effective inhibitors of type 4 prepilin peptidase. High throughput screening assays can also be developed in accordance with well known methodologies to identify these inhibitors. Identified inhibitors are believed to be useful as anti-bacterial agents. These agents are also expected to be useful in inhibiting the cleavage activity of other TFPP-like aspartyl proteases in this subclass which utilize the same cleavage mechanism and/or contain the same active site.

Further, knowledge of the chemical nature of test compounds identified as inhibitors and the target site at which these inhibitors must act on the enzyme to inhibit cleavage activity is useful in the identification and/or design and development of additional inhibitory agents. For example, test compounds with structures known or suspected to target the aspartic acid residues of type 4 prepilin peptidase or to mimic peptides corresponding to the region surrounding the cleavage site of the prepilin substrate can be identified. Alternatively, new test compounds with structures designed to target aspartic acid residues of type 4 prepilin peptidase or to mimic peptides corresponding to the region surrounding the cleavage site of the prepilin substrate can be synthesized. The ability of these test compounds to inhibit cleavage activity of this peptidase is then determined via well known methods. In one embodiment, inhibitory activity is determined via an in vitro cleavage assay such as that described herein. Similar approaches to those used in the design and selection or identification of protease inhibitors for the treatment of HIV can also be utilized in the design and selection or identification of these new anti-bacterial agents.

Test compounds identified as inhibitors of peptidase cleavage activity are believed to be particularly useful as anti-bacterial agents. Pharmaceutical compositions comprising an active test compound and a pharmaceutically acceptable vehicle can be formulated in accordance with well known techniques. The compounds can then be administered to inhibit virulence factor production by bacteria and to inhibit bacterial infections in a host. By "host" it is meant to include humans. Further, it is believed that active test compounds will also be useful in inhibiting development of drug resistant strains of bacteria when administered in combination with a second known therapeutically effective anti-bacterial agent. In this embodiment, it is preferred that the active test compound be administered just prior to or at the same time as the second anti-bacterial agent. Thus, the present invention also relates to compositions comprising a compound which inhibits type 4 prepilin peptidase activity and a second known therapeutically effective anti-bacterial agent.

The following non-limiting examples are provided to further illustrate the claimed invention.

EXAMPLES

Example 1

Membrane Preparation

Membrane preparation protocol was adapted from the cell fractionation protocol described by Pfau (1998. *J. Bact.* 180(17):4724–33). Overnight cultures were placed on ice for 20 minutes, then pelleted at 5000×g for 10 minutes. The cell pellet was resuspended in 1 ml 200 mM Tris pH 8.0 to which 1 ml 50 mM Tris pH 8.0, 1 M sucrose, 2 ml water, 20 $\mu$l 0.5 M EDTA, and 20 $\mu$l lysozyme (10 mg/ml) were added. The cell suspension was allowed to incubate on ice for 30 minutes. Then, 100 $\mu$l 1 M MgSO$_4$ was added and the suspension was pelleted at 5000×g for 10 minutes. The cell pellet was resuspended in 5 ml 50 mM Tris pH 8.0, sonicated 3 times for 15 seconds, and centrifuged at 5000×g for 10 minutes. The supernatant was then centrifuged at 230,000×g for 15 minutes. The resulting pellet, which contained the total membrane fraction was resuspended in 200 $\mu$l 50 mM Tris pH 8.0.

Example 2

TcpA Prepilin Quantitation

Membrane preparations were made from overnight cultures at 42° C. of the *E. coli* K38 that does not express TcpA and *E. coli* K38 p3Z-A, pGP1-2 which overexpresses TcpA prepilin. P3Z-A provides tcpA under the control of a T7 promoter, and GP1-2 provides the heat-inducible T7 RNA polymerase that drives transcription of the tcpA on p3Z-A. Then, 20 $\mu$l of the membrane preparation of K38 and K38 p3Z-A, pGP1-2 along with 3 $\mu$g of trypsin were subjected to electrophoresis on a 12.5% SDS-PAGE gel followed by staining with Coomassie Blue. The stained gel was dried using the NOVEX gel drying system. The dried gel was scanned by a Molecular Dynamics Personal Densitometer SI and the densitometry analysis was performed using ImageQuant version 1.2. The volume of the 3 $\mu$g trypsin band, the TcpA prepilin band, the corresponding location of the TcpA prepilin band in the TcpA negative control lane (K38), and an approximately 28 kDa band from both K38 and K39 p3Z-A, pGP1-2 were measured while adjusting to a single background value. The mass of the TcpA prepilin present in the K30 p3Z-A, pGP1-2 lane was determined by first subtracting the volume of the TcpA prepilin band from the volume of the corresponding area in the K38 TcpA prepilin-lacking lane. This controlled for the staining intensity of minor protein bands that co-migrate with TcpA prepilin. By comparing the volume values from the 28 kDa bands from the TcpA and TcpA-negative lanes a further adjustment was made to the TcpA prepilin value to control for the loading difference between the lanes. The trypsin band volume was divided by 3 $\mu$g to determine a volume/$\mu$g value, which was applied to the final TcpA prepilin band value to determine the $\mu$g TcpA/$\mu$l membrane preparation. The TcpA membrane preparation was diluted with 50 mM Tris buffer to a concentration of 0.2 $\mu$g/$\mu$l.

Example 3

In Vitro Cleavage Assay

A membrane preparation from the *E. coli* strain K38 p3Z-A, pGP1-2, which was determined to contain 0.2 $\mu$g TcpA prepilin/$\mu$l, was the source of prepilin in the in vitro TcpJ proteases assay instead of purified prepilin. A membrane preparation of the TcpJ-expressing strain JM109, pCL9, both wild-type and mutant alleles was the source of the wild-type and mutant TcpJ protein for the in vitro cleavage reactions. The 100 $\mu$l processing reaction is performed by combining a 50 $\mu$l substrate fraction with a 50 $\mu$l enzyme fraction and incubating at 37° C. for 1 hour. The substrate fraction was prepared by combining 5 $\mu$l of the TcpA-containing membrane preparation (1 $\mu$g TcpA), 10 $\mu$l 0.5% w/v cardiolipin, 20 $\mu$l of 2× assay buffer (125 mM triethanolamine HCl pH 7.5, 2.5% v/v Triton-X-100), and brought up to the total volume with water. The enzyme fraction was prepared by combining varying volumes of TcpJ-containing membrane preparation and water to bring the volume to 50 µl. The cleavage reaction was stopped by the addition of 100 µl of 5X protein sample buffer. An increasing range of volumes of the membrane preparation containing wild-type TcpJ was added to the in vitro processing assay in order to determine the amount required to cleave 50% of the 1 µg TcpA included in the assay. This amount of activity was defined as 1 unit of TcpJ cleavage activity.

Example 4

Chemical Inhibitors

Chemical inhibitors were tested for their ability to prevent cleavage of TcpA from the prepilin form to the mature form in the in vitro cleavage assay. Inhibitors were added at specific concentrations to the in vitro assay mixture, which contained 1 unit of TcpJ activity. Inhibitors were added to both enzyme and substrate fractions so that when combined the inhibitor concentration remained constant. The enzyme fraction was allowed to incubate at room temperature for 30 minutes prior to combination of the two fractions. The 100 µl reaction was allowed to proceed for 1 hour at 37° C. before addition of 100 µl of 2×SDS protein sample buffer that stopped the reaction. The specific concentrations of each inhibitor are described in Table 1.

The EDAC/glycinamide inhibition protocol is a two step chemical reaction that modifies carboxylic acid functional groups, such as those that partly make up the R-group of aspartic acid and glutamic acid. This protocol is based on well known procedures set forth for the selective modification of carboxyl groups in proteins. TcpJ containing membranes containing the equivalent of 6 units of TcpJ activity were incubated in 80 µl with 25 mM potassium biphthalate, pH 4.0, and 100 mM EDAC (1-ethyl-3-(3-dimethlaminopropyl)carbodiimide hydrochloride) for 30 minutes at room temperature. Twenty microliters of 1 M glycinamide was added to the mixture and another 30 minute incubation at room temperature was performed before the modification reaction was stopped by the addition of 150 µl of 200 mM Tris buffer, pH 8. The mixture was dialyzed against 50 mM Tris buffer, pH 8, for 1 hour and then centrifuged at 230,000×g (60,000 rpm in TLA 100.3 rotor) for 15 minutes. The resulting membrane pellet, which contains the chemically modified TcpJ, was resuspended in 60 µl 50 mM Tris, pH 8. Twenty microliters of the membrane suspension was subjected to the in vitro peptidase assay to determine the peptidase activity. Activity of the modified TcpJ was compared to an equivalent amount of TcpJ that had been subjected to a mock modification procedure which did not include EDAC or glycinamide.

What is claimed is:

1. A method of designing inhibitors of type 4 prepilin peptidase (TFPP)-like aspartyl protease enzymes comprising:
   (a) synthesizing a compound which targets aspartic acid residues of an enzymatic active site of a TFPP-like aspartyl protease enzyme or mimics a region surrounding a cleavage site of a TFPP-like aspartyl protease substrate; and (b) determining the ability of the synthesized compound to inhibit cleavage activity of the TFPP-like aspartyl protease enzyme.

2. The method of claim 1 wherein the TFPP-like aspartyl protease enzyme is a type 4 prepilin peptidase.

3. The method of claim 2 wherein the ability of the synthesized compound to inhibit cleavage activity is determined via a method comprising:

(a) preparing a membrane fraction from a bacterial strain expressing a type 4 prepilin peptidase;

(b) contacting the membrane fraction with the synthesized compound; and (c) determining cleavage activity of the type 4 prepilin peptidase in the presence of the synthesized compound, wherein a decrease of the cleavage activity of the type 4 prepilin peptidase in the presence of the synthesized compound as compared to the activity of type 4 prepilin peptidase in the absence of the synthesized compound is indicative of the test compound being an inhibitor of type 4 prepilin peptidase.

4. A method of identifying potential inhibitors of TFPP-like aspartyl protease enzymes comprising:
(a) selecting a test compound having a structure known to or suspected of targeting aspartic acid residues or mimicking a region surrounding a cleavage site of a TFPP-like aspartyl protease substrate; and
(b) determining the ability of the identified test compound to inhibit cleavage activity of the TFPP-like aspartyl protease enzyme.

5. The method of claim 4 wherein the TFPP-like aspartyl protease enzyme is a type 4 prepilin peptidase.

6. A mutant construct of TcpJ wherein an amino acid at position 18, 46, 48, 51, 65, 73, 76, 81, 88, 125, 172, 183, 189, 191, 212, or 213 of SEQ ID NO:4 is mutated.

7. The mutant construct of claim 6 wherein the amino acid is mutated to alanine or leucine.

8. The mutant construct of claim 6 wherein the amino acid at position 125 or 189 of SEQ ID NO: 4 is mutated to asparagine or glutamic acid.

9. The mutant construct of claim 6 wherein the amino acid at position 183 of SEQ ID NO:4 is mutated to asparagine.

10. A nucleic acid sequence encoding a type 4 prepilin peptidase homologue in *Staphylococcus aureus* comprising SEQ ID NO:2.

11. The nucleic acid sequence of claim 10 comprising SEQ ID NO:1.

* * * * *

SEQUENCE LISTING

<160> NUMBER OF SEQ ID NOS: 4

<210> SEQ ID NO 1
<211> LENGTH: 705
<212> TYPE: DNA
<213> ORGANISM: Staphylococcus aureus

<400> SEQUENCE: 1

```
ttggtagtat tgttatctta tagttgcagt tgtattttta gttttctata tcaatttata      60
tctatagaag aaacgtcatt tgattattta catagaagat cgaaatgtga ttattgtaat     120
tcgtcactca aatggtatga attaatgccg attattagtt ttttattatt aaaagggcga     180
tgtcgaaact gtcgaaagcg tatttcccta acacatttct tagggggaaac ctttgcttta     240 atacctatcg tctttattaa gtatgatttc acatacgtaa atgctacgct atttataact     300
acatatgttt ttctgcttat ttttactatg accgatatca cttctttaat gttagattgt     360
cgcttaatta taatttattg tatcgtttct ctctcgttaa gtatgattta tccagtagct     420
tttatcatta ttagtatgac cacgcatata ttctactttt tatttcgggc atatattggt     480
tatggtgacg ttttactaat atctgcactt tctttgtttt tccctctcca attcactatt     540
tatgtcattt tatttacatt tgtcattgct ggtttagttg ctttaattac catgatattt     600
aagccgatta aactattacc ccttgttcca tttatattta tttcctttt tatcaattca     660 cttttttata atgatatcca tcaattttta ggaggcgtat atttt               705
```

<210> SEQ ID NO 2
<211> LENGTH: 235
<212> TYPE: PRT
<213> ORGANISM: Staphylococcus aureus

<400> SEQUENCE: 2

Leu Val Val Leu Leu Ser Tyr Ser Cys Ser Cys Ile Phe Ser Phe Leu

|   |   | 1 |   |   |   | 5 |   |   |   | 10 |   |   |   | 15 |   |
|---|---|---|---|---|---|---|---|---|---|---|---|---|---|---|---|

Tyr Gln Phe Ile Ser Ile Glu Glu Thr Ser Phe Asp Tyr Leu His Arg
  1               5                  10                 15
        20                  25                  30

Arg Ser Lys Cys Asp Tyr Cys Asn Ser Ser Leu Lys Trp Tyr Glu Leu
        35                  40                  45

Met Pro Ile Ile Ser Phe Leu Leu Lys Gly Arg Cys Arg Asn Cys
        50                  55                  60

Arg Lys Arg Ile Ser Leu Thr His Phe Leu Gly Glu Thr Phe Ala Leu
 65                 70                  75                  80

Ile Pro Ile Val Phe Ile Lys Tyr Asp Phe Thr Tyr Val Asn Ala Thr
                85                  90                  95

Leu Phe Ile Thr Thr Tyr Val Phe Leu Leu Ile Phe Thr Met Thr Asp
                100                 105                 110

Ile Thr Ser Leu Met Leu Asp Cys Arg Leu Ile Ile Tyr Cys Ile
        115                 120                 125

Val Ser Leu Ser Leu Ser Met Ile Tyr Pro Val Ala Phe Ile Ile Ile
130                 135                 140

Ser Met Thr Thr His Ile Phe Tyr Phe Leu Phe Arg Ala Tyr Ile Gly
145                 150                 155                 160

Tyr Gly Asp Val Leu Leu Ile Ser Ala Leu Ser Leu Phe Phe Pro Leu
                165                 170                 175

Gln Phe Thr Ile Tyr Val Ile Leu Phe Thr Phe Val Ile Ala Gly Leu
                180                 185                 190

Val Ala Leu Ile Thr Met Ile Phe Lys Pro Ile Lys Leu Leu Pro Leu
                195                 200                 205

Val Pro Phe Ile Phe Ile Ser Phe Phe Ile Asn Ser Leu Phe Tyr Asn
        210                 215                 220

Asp Ile His Gln Phe Leu Gly Gly Val Tyr Phe
225                 230                 235

<210> SEQ ID NO 3
<211> LENGTH: 986
<212> TYPE: DNA
<213> ORGANISM: Vibrio cholerae

<400> SEQUENCE: 3
gaattcaaaa taaacagat tgcatatcag tctgggtttg ctagcgtttc atatttttct      60
acagtattta agtcaaccat gaatgtagca ccaagtgaat atttatttat gttgacagga     120
gttgcagaaa aataatggaa tacgtttact tgatcctatt ttcgattgta tcactgattt     180
tgggtagttt tagtaatgtt gtgatttatc gtctaccaag aaaaatttta ctaaagaatc     240
atttttttta tgacatcgat tcaaatcgtt ccatgtgccc taaatgtgga aataaaatca     300
gttggtatga taatgttcca ttgttaagtt atttgttact tcatggtaag tgtagacatt     360
gtgatgaaaa aatttcatta agttatttta ttgtcgagtt atcatttttt ataatcgcat     420
ttccaatata ttggttatca actgactggg ttgattcgtt cgtattgctc gggctttact     480
ttattttatt caatcttttt gtaattgatt taaatctat gctattgcca aatttactta     540
cgtatccgat attcatgttg gcatttattt atgtgcagcc aaatcaagca ttaacagttg     600
aaagctctat tattggtggt tttgcggctt tcatcattac ctatgtgagt aatttcattg     660
ttcggttatt caaaagaatc gatgtgatgg gaggtggaga tataaagctc tatactgcga     720
ttggtactct tatcggtgtt gagtttgtac catatttatt cttgctgtcc tcgattattg     780
catttattca ttggttttttt gctagagtct catgtcggta ttgcttatat atccctcttg     840

```
gaccaagcat tattatctct tttgtaattg ttttttttc aatccgttta atgtgagcta    900
aaatgaagtt ttctatcaag ttactaatga tttttacatc aattataatt actatttcat    960
ctatccttac ttactttcag atgcat                                         986
```

<210> SEQ ID NO 4
<211> LENGTH: 253
<212> TYPE: PRT
<213> ORGANISM: Vibrio cholerae

<400> SEQUENCE: 4

```
Met Glu Tyr Val Tyr Leu Ile Leu Phe Ser Ile Val Ser Leu Ile Leu
 1               5                  10                  15

Gly Ser Phe Ser Asn Val Val Ile Tyr Arg Leu Pro Arg Lys Ile Leu
                20                  25                  30

Leu Lys Asn His Phe Phe Tyr Asp Ile Asp Ser Asn Arg Ser Met Cys
            35                  40                  45

Pro Lys Cys Gly Asn Lys Ile Ser Trp Tyr Asp Asn Val Pro Leu Leu
        50                  55                  60

Ser Tyr Leu Leu Leu His Gly Lys Cys Arg His Cys Asp Glu Lys Ile
 65                 70                  75                  80

Ser Leu Ser Tyr Phe Ile Val Glu Leu Ser Phe Phe Ile Ile Ala Phe
                85                  90                  95

Pro Ile Tyr Trp Leu Ser Thr Asp Trp Val Asp Ser Phe Val Leu Leu
            100                 105                 110

Gly Leu Tyr Phe Ile Leu Phe Asn Leu Phe Val Ile Asp Phe Lys Ser
        115                 120                 125

Met Leu Leu Pro Asn Leu Leu Thr Tyr Pro Ile Phe Met Leu Ala Phe
130                 135                 140

Ile Tyr Val Gln Pro Asn Gln Ala Leu Thr Val Glu Ser Ser Ile Ile
145                 150                 155                 160

Gly Gly Phe Ala Ala Phe Ile Ile Thr Tyr Val Ser Asn Phe Ile Val
                165                 170                 175

Arg Leu Phe Lys Arg Ile Asp Val Met Gly Gly Gly Asp Ile Lys Leu
            180                 185                 190

Tyr Thr Ala Ile Gly Thr Leu Ile Gly Val Glu Phe Val Pro Tyr Leu
        195                 200                 205

Phe Leu Leu Ser Ser Ile Ile Ala Phe Ile His Trp Phe Ala Arg
    210                 215                 220

Val Ser Cys Arg Tyr Cys Leu Tyr Ile Pro Leu Gly Pro Ser Ile Ile
225                 230                 235                 240

Ile Ser Phe Val Ile Val Phe Phe Ser Ile Arg Leu Met
                245                 250
```